(12) United States Patent
Pinza et al.

(10) Patent No.: US 7,435,812 B2
(45) Date of Patent: Oct. 14, 2008

(54) METHOD FOR PREPARING A GLUCOSAMINE COMPOUND AND COMPOUND THUS OBTAINED

(75) Inventors: Mario Pinza, Corsico (IT); Franca Segnalini, Latina (IT); Marcello Marchetti, Rome (IT); Tommaso Iacoangeli, Rome (IT); Francesco De Vita, Aprilia (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 340 days.

(21) Appl. No.: 10/499,293

(22) PCT Filed: Dec. 2, 2002

(86) PCT No.: PCT/EP02/13570

§ 371 (c)(1),
(2), (4) Date: Jan. 10, 2005

(87) PCT Pub. No.: WO03/055897

PCT Pub. Date: Jul. 10, 2003

(65) Prior Publication Data

US 2005/0171058 A1 Aug. 4, 2005

(30) Foreign Application Priority Data

Dec. 28, 2001 (IT) .................. MI2001A2818

(51) Int. Cl.
*C07H 1/00* (2006.01)
*C07H 5/06* (2006.01)

(52) U.S. Cl. ...................... 536/55.2; 514/62

(58) Field of Classification Search ............ 514/62; 536/55.2

See application file for complete search history.

(56) References Cited

U.S. PATENT DOCUMENTS

| 4,642,340 | A | 2/1987 | Makovec et al. |
| 5,847,107 | A * | 12/1998 | De Wan et al. ............. 536/55.3 |
| 5,902,801 | A | 5/1999 | Chopdekar et al. |
| 6,812,223 | B2 | 11/2004 | Mukhopadhyay et al. |

FOREIGN PATENT DOCUMENTS

| EA | 2003-00614 A1 | 10/2004 |
| EP | 214 642 | 3/1987 |
| WO | WO 02/43653 * | 6/2002 |
| WO | WO 02/43653 A2 | 6/2002 |

OTHER PUBLICATIONS

Robert Breuer, "Ueber das freie chitosamin", Chem. Ber., vol. 31, pp. 2193-2200 1898. Considered discussion of this at p. 1 of specification only.

* cited by examiner

*Primary Examiner*—Shaojia Anna Jiang
*Assistant Examiner*—Ganapathy Krishnan
(74) *Attorney, Agent, or Firm*—Oblon, Spivak, McClelland, Maier & Neustadt, P.C.

(57) ABSTRACT

Method for preparing a compound comprising protonated glucosamine and Cl⁻, Na⁺ and $SO_4^{2-}$ ions, in which (a) glucosamine hydrochloride and a stoichiometric excess of sodium sulphate are placed in water, (b) the mixture obtained from the preceding step (a) is heated, (c) the mixture is cooled, and (d) the solid present in the said cooled mixture is recovered by filtration. Compound comprising protonated glucosamine and Cl⁻, Na⁺ and $SO_4^{2-}$ ions and having the X-ray diffraction diagram of FIG. 1.

13 Claims, 1 Drawing Sheet

METHOD FOR PREPARING A GLUCOSAMINE COMPOUND AND COMPOUND THUS OBTAINED

BACKGROUND OF THE INVENTION

1. Field of the Invention

Figure 1:
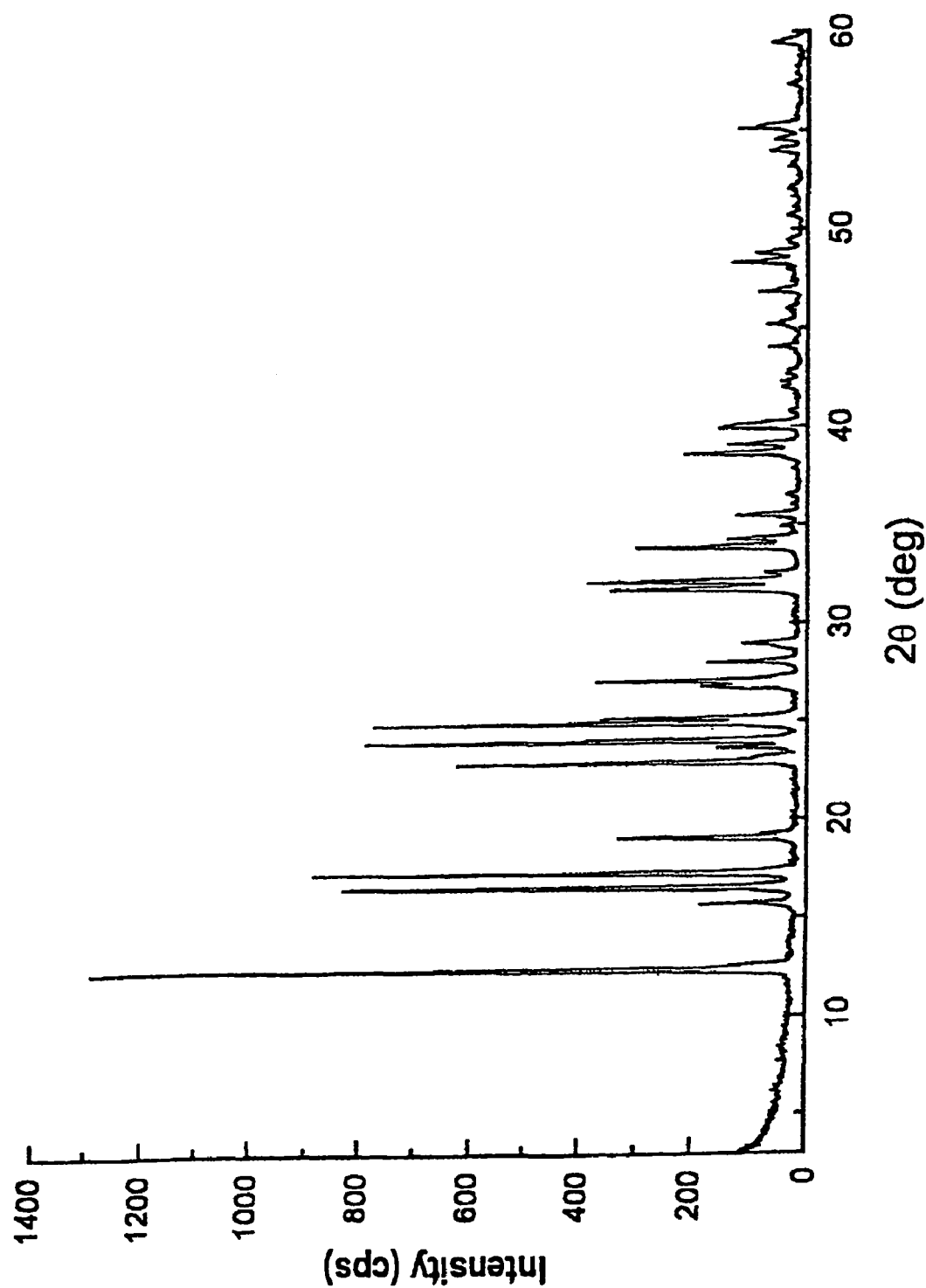

The present invention relates to a method for preparing a glucosamine compound, and to a compound thus obtained.

2. Description of the Background

As is known, glucosamine (2-amino-2-deoxyglucose; chitosamine; $GluNH_2$) is a component of mucoproteins and mucopolysaccharides. It is usually obtained from chitin and is isolated as the hydrochloride.

Glucosamine sulphate is a drug that is well known and widely used in the treatment of rheumatic fever, arthritic and arthrosic complaints, both acute and chronic, and in the treatment of pathological conditions originating from metabolic disorders of osteoarticular tissue. Its synthesis was described at the end of 1898 by Breuer (Chem. Ber. 31, 2197). However, its physicochemical properties are such that it is relatively difficult to handle and occasionally unstable. The main problems are derived from its high hygroscopicity.

U.S. Pat. No. 4,642,340 teaches how to overcome this drawback by using a presumed mixed salt of formula A:

$$[GluNH_3^+]_2 \cdot 2Na^+ \cdot SO_4^{2-} \cdot 2Cl^- \qquad A$$

which is in the form of crystalline powder, melts at more than 300° C., is stable under ambient conditions and has pharmacological properties that are substantially identical to those of glucosamine sulphate.

The said document also describes the preparation of the said presumed mixed salt A, by:
(a) dissolving, with stirring, anhydrous sodium chloride in 5.5-7.5 parts by weight of distilled water for each part of sodium chloride at a temperature of from 50° C. to 70° C.;
(b) dissolving, with stirring, in the solution obtained in step (a), a stoichiometric amount of glucosamine sulphate at a temperature of from 35° C. to 45° C.;
(c) precipitating the presumed mixed salt A by adding a precipitating liquid that is water-miscible and in which the presumed mixed salt A has a solubility not greater than 0.1% (w/v), this step being performed with stirring at a temperature of from 40° C. to 50° C.;
(d) completing the precipitation by reducing the temperature of the mixture; and
(e) recovering the presumed precipitated mixed salt A.

The precipitating liquid used in step (c) is acetone, ethanol, acetonitrile, tetrahydrofuran or dioxane.

A similar method is described in U.S. Pat. No. 5,847,107. According to this method, the said presumed mixed salt A is obtained by:
(a) dissolving glucosamine hydrochloride and sodium sulphate, in stoichiometric amounts, in water; and
(b) precipitating the presumed mixed salt A by adding a precipitating liquid that is water-miscible.

In this case also, the precipitating liquid used is acetone, ethanol, acetonitrile, tetrahydrofuran or dioxane.

Another similar method is described in EP-A-0 214 642. According to this method, the said presumed mixed salt A and other similar products are obtained by:
(a) forming glucosamine sulphate from glucosamine and sulphuric acid in water;
(b) forming the presumed mixed salt A by adding an approximately stoichiometric amount of an alkali metal halide or alkaline-earth metal halide; and
(c) precipitating the presumed mixed salt A by adding a water-soluble solvent.

The precipitating solvents mentioned are ethanol, acetone and acetonitrile.

According to U.S. Pat. No. 5,902,801, the product present on the market is not thought to be a true mixed salt A, but rather a simple stoichiometric mixture of glucosamine hydrochloride and sodium sulphate (column 1, lines 23-29). This document describes a compound that purports to be novel and to be the true mixed salt A. According to this document, the true mixed salt A is that obtained by (column 3, lines 5-19):
(a) placing stoichiometric amounts of glucosamine hydrochloride and sodium sulphate in contact in a sufficient amount of water to have a solids concentration of from about 15 to 40% by weight (this step takes from 15 minutes to 2 hours and is carried out at a temperature of from about 20° C. to about 40° C.); and
(b) removing the water by freeze-drying at a pressure below 800 milliTorr, preferably from 300 to 500 milliTorr, and at a temperature from −60° C. to 0° C. and preferably from −40° C. to −5° C.

However, the water is not totally removed and the mixed salt A thus obtained contains from 3 to 5% by weight of water (column 2, lines 20-24).

The abovementioned known methods thus involve the use of starting materials in one of the exact stoichiometric ratios given below:

$$[GluNH_2]_2 \cdot H_2SO_4 + 2NaCl \rightarrow A \qquad \text{Eq. 1}$$

$$[GluNH_2 \cdot HCP]_2 + H_2SO_4 \rightarrow A \qquad \text{Eq. 2}$$

A person skilled in the art will readily appreciate that the abovementioned prior art methods have considerable drawbacks.

Specifically, in the methods of U.S. Pat. No. 4,642,340, U.S. Pat. No. 5,847,107 and EP-A-0 214 642, the precipitation requires the use of organic solvents and this obliges the application of specific safety standards on account of their flammability and explosiveness. In addition, a specific treatment of the wastes is necessary before discharging. This therefore involves factors that, in addition to having an impact on the safety of the industrial production, also involve increases in the production costs. Finally, a further drawback is given by the fact that the organic solvents cannot be completely removed from the presumed mixed salt A either during the drying operation.

As regards the freeze-drying process required in the method of U.S. Pat. No. 5,902,801, in addition to being expensive, it does not allow the impurities present in the initial solution to be removed. The mixed salt A thus obtained actually retains all the abovementioned impurities. To overcome this drawback, the glucosamine hydrochloride and the sodium sulphate will have to be very pure and, therefore, very expensive. Finally, small amounts of water also tend to remain in the mixed salt A in the freeze-drying process.

SUMMARY OF THE INVENTION

It has now been found, surprisingly, that all the abovementioned drawbacks are overcome by working in water alone.

In a first aspect, the present invention thus comprises a method for preparing a compound comprising protonated glucosamine and $Cl^-$, $Na^+$ and $SO_4^{2-}$ ions in the ratio indicated in the following formula:

$$[GluNH_3^+]_2 \cdot 2Na^+ \cdot SO_4^{2-} \cdot 2Cl^- \qquad A$$

the method being carried out by:
(a) placing glucosamine hydrochloride and a stoichiometric excess of sodium sulphate in water, (b) heating the mixture obtained in the preceding step (a),
(c) cooling the mixture, and
(d) recovering the solid present in the said cooled mixture by filtration.

DETAILED DESCRIPTION OF THE PREFERRED EMBODIMENTS

Preferably, in step (a), from 0.8 to 1 mol of sodium sulphate is used per mole of glucosamine hydrochloride. Even more preferably, 0.9 mol of sodium sulphate is used per mole of glucosamine hydrochloride.

Advantageously, the amount of water used in step (a) ranges from 180 to 230 ml per mole of glucosamine hydrochloride. Preferably, the amount of water is about 200 ml per mole of glucosamine hydrochloride.

In step (b), the mixture is preferably heated, with stirring, to a temperature of from 35° C. to 55° C. and even more preferably to a temperature of from 40° C. to 45° C.

The heating in step (b) is preferably continued for a period of from 15 minutes to 5 hours and even more preferably from 2.5 to 3.5 hours.

In step (c), the mixture is preferably cooled to a temperature of from 0° C. to 33° C. and even more preferably to about 30° C.

The cooling in step (c) is preferably continued for a period of from 1 to 5 hours and even more preferably from 2.5 to 3.5 hours.

The solid collected by filtration in step (d) is dried in a vacuum oven or under a stream of air according to standard techniques.

Another advantage of the present invention is that, by always working only in water, the mother liquors obtained from the filtration in step (d) are readily recycled. In this way, the yield for the method is very close to the theoretical yield.

Since the method of the present invention is based on a filtration of saturated solution, a person skilled in the art will readily appreciate that the concentrations, temperatures and times previously indicated are not limiting. For example, the stoichiometric excess of the sodium sulphate can vary within a wide range depending on the amount of water used and the filtration temperature.

The glucosamine compound according to the present invention is of very high purity, does not contain excess sulphates, is virtually anhydrous and can be dried by simple removal of the final traces of moisture.

In addition, as shown in FIG. 1, it has a specific and characteristic X-ray diffraction diagram.

The X-ray diffraction measurements were carried out using a Selfert XRD3000 powder diffractometer with Cu-k$\alpha$ radiations ($\lambda$=1.5406 Å). The diffractometer was equipped with a secondary graphite monochromator (between the sample and the detector), the incident beam was limited by entry slits of from 3 to 2 mm, and the diffracted beam was limited by detector slits of from 0.3 to 0.2 mm.

The diffraction diagram was acquired with "scan $\theta$-2$\theta$" in the range $3 \leq 2\theta \leq 60°$, with a sweep size of 0.04° and a count time of 4 sec/sweep.

The examples that follow serve to illustrate the invention without, however, limiting it.

EXAMPLE 1

Preparation of the Glucosamine According to the Present Invention 116.28 g (0.54 mol) of glucosamine hydrochloride and 69.47 g (0.49 mol) of anhydrous sodium sulphate were added to 109 ml of water with stirring. The mixture was heated to 42° C.-45° C. and then maintained at this temperature for 3 hours with stirring. The mixture was cooled to 30° C. over 30 minutes and maintained at this temperature for a further 3 hours with stirring.

The precipitated solid was collected by filtration and dried at 50° C. under reduced pressure, to constant weight.

114.7 g (74.1% of the theoretical yield) of the glucosamine compound according to the present invention were thus obtained in the form of a white crystalline powder which, on analysis, gave the results shown in Table I.

The mother liquors filtered off (166 g) consisted of water (100.4 ml), glucosamine hydrochloride (27.74 g; 0.13 mol) and sodium sulphate (37.90 g; 0.27 mol).

TABLE I

| Elemental analysis | Theoretical | Result |
|---|---|---|
|  | C = 25.14% | C = 25.10% |
|  | H = 4.92% | H = 4.85% |
|  | N = 4.88% | N = 4.70% |
| Glucosamine |  | 100.2% |
| Cl$^-$ |  | 99.8% |
| SO$_4^{2-}$ |  | 100.5% |
| Optical rotation |  | $[\alpha]^{20}_D = +52.6$ |

The glucosamine content was determined by potentiometric titration with NaOH (0.1 N) and by determining the equivalent point with a glass electrode.

The content of Cl$^-$ was determined by potentiometric titration with silver nitrate (0.05 N) and the equivalent point was determined with an Ag/AgCl electrode.

The SO$_4^{2-}$ content was determined by ionic chromatography using a DIONEX™ AG-9 analytical column with conductimetric detection and external standardization.

The optical rotation was determined according to Ph. Eur. IV Ed. Par. (2.2.7) 2002, using a 1 dm polarimeter tube after an equilibration time of 3 hours at room temperature (c=10% in water).

EXAMPLE 2

First Recycling of the Mother Liquors

Water (8.45 ml), glucosamine hydrochloride (88.54 g; 0.41 mol) and sodium sulphate (31.59 g; 0.22 mol) were added to the mother liquors obtained from Example 1, and the process was performed as described in Example 1.

After drying, 117.79 g (76.1% of the theoretical yield) of the glucosamine compound according to the present invention were obtained in the form of a white crystalline powder which, on analysis, gave results similar to those of Table I.

The combined yield for the two preparations, calculated on the basis of the total number of moles of glucosamine used in the two preparations described in Examples 1 and 2 was 85.4%.

EXAMPLE 3

Second Recycling of the Mother Liquors

Water (8.45 ml), glucosamine hydrochloride (88.54 g; 0.41 mol) and sodium sulphate (31.59 g; 0.22 mol) were added to the mother liquors obtained from Example 2, and the process was performed as described in Example 2.

After drying, 117.2 g (75.8% of the theoretical yield) of the glucosamine compound according to the present invention were obtained in the form of a white crystalline powder which, on analysis, gave results similar to those of Table I.

The combined yield for the three preparations, calculated on the basis of the total number of moles of glucosamine used in the three preparations described in Examples 1, 2 and 3, was 89.6%.

The invention claimed is:

1. A method for preparing a compound comprising protonated glucosamine and $Cl^-$, $Na^+$ and $SO_4^{2-}$ ions in the ratio indicated in the following formula (A):

$$[GluNH_3^+]_2 \cdot 2Na^+ \cdot SO_4^{2-} \cdot 2Cl^- \qquad A$$

wherein the method comprises:
(a) placing glucosamine hydrochloride and a stoichiometric excess of sodium sulphate in water, thereby obtaining a mixture,
(b) heating the mixture,
(c) cooling the mixture, and
(d) recovering the solid present in the cooled mixture by filtration.

2. A method according to claim 1, wherein in step (a), from 0.8 to 1 mol of sodium sulphate is used per mole of glucosamine hydrochloride.

3. A method according to claim 2, wherein in step (a), 1 mol of sodium sulphate is used per mole of glucosamine hydrochloride.

4. A method according to claim 1, wherein the amount of water in step (a) ranges from 180 to 230 ml per mole of glucosamine hydrochloride.

5. A method according to claim 4, wherein the amount of water is about 200 ml per mole of glucosamine hydrochloride.

6. A method according to claim 1, wherein in step (b), the mixture is heated to a temperature ranging from 35° C. to 55° C.

7. A method according to claim 6, wherein the mixture is heated to a temperature ranging from 40° C. to 45° C.

8. A method according to claim 1, wherein in step (b), the heating is continued for a period ranging from 15 minutes to 5 hours.

9. A method according to claim 8, wherein the heating is continued for a period ranging from 2.5 to 3.5 hours.

10. A method according to claim 1, wherein in step (c), the mixture is cooled to a temperature ranging from 0° C. to 33° C.

11. A method according to claim 10, wherein the mixture is cooled to about 30° C.

12. A method according to claim 1, wherein in step (c), the cooling is continued for a period ranging from 1 to 5 hours.

13. A method according to claim 12, wherein the cooling is continued for a period ranging from 2.5 to 3.5 hours.

* * * * *

UNITED STATES PATENT AND TRADEMARK OFFICE
CERTIFICATE OF CORRECTION

PATENT NO. : 7,435,812 B2  Page 1 of 1
APPLICATION NO. : 10/499293
DATED : October 14, 2008
INVENTOR(S) : Pinza et al.

It is certified that error appears in the above-identified patent and that said Letters Patent is hereby corrected as shown below:

Title Page, Item [*] Notice:
Delete the phrase "by 340 days" and insert -- by 759 days --.

Signed and Sealed this

Tenth Day of August, 2010

David J. Kappos
*Director of the United States Patent and Trademark Office*